(12) United States Patent
Grohowski, Jr.

(10) Patent No.: US 9,089,427 B2
(45) Date of Patent: Jul. 28, 2015

(54) METHOD OF MAKING POROUS METAL ARTICLES

(75) Inventor: Joseph A. Grohowski, Jr., Glens Falls, NY (US)

(73) Assignee: Praxis Powder Technology, Inc., Queensbury, NY (US)

(*) Notice: Subject to any disclaimer, the term of this patent is extended or adjusted under 35 U.S.C. 154(b) by 930 days.

(21) Appl. No.: 13/270,657

(22) Filed: Oct. 11, 2011

(65) Prior Publication Data

US 2012/0065739 A1    Mar. 15, 2012

Related U.S. Application Data

(63) Continuation-in-part of application No. 12/688,505, filed on Jan. 15, 2010, now abandoned, which is a continuation of application No. 10/884,444, filed on Jul. 2, 2004, now Pat. No. 7,674,426.

(51) Int. Cl.
*A61F 2/30* (2006.01)
*A61L 27/04* (2006.01)
(Continued)

(52) U.S. Cl.
CPC ......... *A61F 2/30767* (2013.01); *A61F 2/30771* (2013.01); *A61L 27/04* (2013.01); *A61L 27/427* (2013.01); *A61L 27/56* (2013.01); *B01D 39/2093* (2013.01); *B22F 3/1109* (2013.01); *B22F 3/1121* (2013.01); *B22F 3/225* (2013.01); *B29C 43/006* (2013.01); *A61F 2/3094* (2013.01); *A61F 2/32* (2013.01); *A61F 2/34* (2013.01); *A61F 2/36* (2013.01); *A61F 2/3662* (2013.01);

(Continued)

(58) Field of Classification Search
CPC ............................ A61F 2/30767; A61L 27/04
USPC ........................................................ 623/18.11
IPC ........... B22F 3/1121, 2001/0066; A61K 9/2054
See application file for complete search history.

(56) References Cited

U.S. PATENT DOCUMENTS 2,672,415 A    3/1954  Balke
3,138,857 A    6/1964  Kuchek
(Continued)

FOREIGN PATENT DOCUMENTS

WO       01/19556 A1    3/2001
WO    2004/039748 A1    5/2004

OTHER PUBLICATIONS

Laptev et al., "Study of Production Route for Titanium Parts Combining Very High Porosity and Complex Shape", Powder metallurgy, vol. 47, No. 1, 2004, pp. 85-92.
(Continued)

*Primary Examiner* — Weiping Zhu
(74) *Attorney, Agent, or Firm* — Charney IP Law LLC (57) ABSTRACT

In one embodiment, the present invention may be a method of making a porous biocompatible metal article by combining a metal powder with a homogenizing aid to form metal granules, including blending the metal granules and an extractable particulate to form a composite, forming the composite into a green article, removing the extractable particulate from the green article to form a metal matrix and pore structure, and sintering the metal matrix and pore structure. Furthermore the present invention may include a second homogenizing aid combined with the extractable particulate. The present invention also includes shaping the metal matrix and pore structure with or without the use of a binder.

35 Claims, 8 Drawing Sheets

(51) Int. Cl.

| | |
|---|---|
| *A61L 27/56* | (2006.01) |
| *B01D 39/20* | (2006.01) |
| *B22F 3/11* | (2006.01) |
| *B22F 3/22* | (2006.01) |
| *B29C 43/00* | (2006.01) |
| *A61L 27/42* | (2006.01) |
| *A61F 2/32* | (2006.01) |
| *A61F 2/34* | (2006.01) |
| *A61F 2/36* | (2006.01) |
| *B22F 1/00* | (2006.01) |
| *B29L 31/00* | (2006.01) |

(52) U.S. Cl.
CPC ............... *A61F 2002/30011* (2013.01); *A61F 2002/30929* (2013.01); *A61F 2002/30957* (2013.01); *A61F 2002/30968* (2013.01); *A61F 2250/0023* (2013.01); *A61F 2310/00017* (2013.01); *A61F 2310/00023* (2013.01); *A61F 2310/00029* (2013.01); *A61F 2310/00047* (2013.01); *A61F 2310/00071* (2013.01); *A61F 2310/00077* (2013.01); *A61F 2310/00095* (2013.01); *A61F 2310/00131* (2013.01); *A61L 2430/02* (2013.01); *B01D 2239/10* (2013.01); *B22F 2001/0066* (2013.01); *B22F 2998/00* (2013.01); *B22F 2999/00* (2013.01); *B29L 2031/7532* (2013.01)

(56) References Cited

U.S. PATENT DOCUMENTS

| | | | |
|---|---|---|---|
| 3,362,818 | A | 1/1968 | Schwarzkopf et al. |
| 3,802,878 | A | 4/1974 | Lindstrom |
| 3,852,045 | A | 12/1974 | Wheeler et al. |
| 4,588,540 | A | 5/1986 | Kiefer et al. |
| 4,765,950 | A | 8/1988 | Johnson |
| 6,008,281 | A | 12/1999 | Yang et al. |
| 6,022,509 | A | 2/2000 | Matthews et al. |
| 6,174,493 | B1 | 1/2001 | Asbury |
| 6,582,470 | B1 | 6/2003 | Lee et al. |
| 6,592,787 | B2 * | 7/2003 | Pickrell et al. ............... 264/44 |
| 6,660,224 | B2 | 12/2003 | Lefebvre et al. |
| 6,846,862 | B2 | 1/2005 | Schofalvi et al. |
| 7,674,426 | B2 | 3/2010 | Grohowski, Jr. |
| 2002/0086039 | A1 | 7/2002 | Lee et al. |
| 2002/0151985 | A1 | 10/2002 | Kuberasampath et al. |
| 2002/0153348 | A1 | 10/2002 | Say et al. |
| 2003/0044301 | A1 | 3/2003 | Lefebvre et al. |
| 2003/0153981 | A1 | 8/2003 | Wang et al. |
| 2004/0072010 | A1 | 4/2004 | Date et al. |
| 2004/0254419 | A1 * | 12/2004 | Wang et al. ............... 600/8 |
| 2005/0207929 | A1 | 9/2005 | Yamada |
| 2006/0002810 | A1 | 1/2006 | Grohowski, Jr. |
| 2006/0003179 | A1 | 1/2006 | Wang et al. |
| 2010/0094420 | A1 | 4/2010 | Grohowski, Jr. |
| 2010/0180724 | A1 | 7/2010 | Grohowski, Jr. |

OTHER PUBLICATIONS

Hens, "Thermat expands precision PIM operation", PM Special Feature, Elsevier Science Ltd., 1998, 3 pages.
Extended European Search Report received for EP Patent Application No. 05763915.5, mailed on Jun. 14, 2010, 9 pages.
International Search Report and Written Opinion for PCT Application No. PCT/US2007/013416, mailed on Nov. 21, 2007, 6 pages.
International Search Report and Written Opinion for PCT Application No. PCT/US2005/023118, mailed on Oct. 24, 2005, 8 pages.

* cited by examiner

METHOD OF MAKING POROUS METAL ARTICLES

CROSS REFERENCE TO RELATED APPLICATIONS

This application is a Continuation-in-Part of U.S. patent application Ser. No. 12/688,505, filed Jan. 15, 2010, and entitled "POROUS METAL ARTICLES HAVING A PREDETERMINED PORE CHARACTER", which is a Continuation of U.S. patent application Ser. No. 10/884,444, filed Jul. 2, 2004, and entitled "POROUS METAL ARTICLES HAVING A PREDETERMINED PORE CHARACTER", the entire specification of each of which is hereby incorporated by reference herein for all purposes.

BACKGROUND OF THE INVENTION

This invention relates to porous metal articles having tailored porosity and methods of manufacturing such articles by using extractable particulates.

Porous metal articles are used in many applications including orthopedic implants, bone growth media, filters, sound suppression materials, fuel cells, catalyst supports, and magnetic shielding. Such porous articles may have open or closed porosity as well as a wide range of pore size, shape, density, and distribution. The specific structures and properties required depend on the application. Known methods of manufacturing porous metals include formation by foaming, diffusion bonding or sintering of powders, depositing a material upon a porous substrate, use of vaporizing materials, and plasma etching.

Foaming describes the creation of porosity through the introduction of some agent, organic or inorganic, that creates voids during the forming process. Diffusion bonding or sintering processes create partially dense networks of powder particles and pores. Porous metal can be formed by the deposition of the desired metal onto a foam or substrate material. This deposition may be accomplished by a number of methods including dipping the substrate material in slurry containing metal powder, evaporation and condensation of the material on the substrate.

When using a vaporizing material as a void former in metals, the material is removed thermally, and the metal matrix material can easily become contaminated by the vaporizing material when the article is exposed to the necessary high processing temperatures. The evolution of the products of decomposition and the vaporized materials are difficult to control which reduces the robustness of the process, thus limiting processing capabilities to articles having smaller cross-sections. Complications resulting from oxidation and other contamination in thermal decomposition or sublimation approaches make such processes not suitable for high-purity applications such as bone implants. In addition, the heat and high pressure of the compaction and densification processes will deform the void former material, thereby not allowing the tailoring of pore properties.

The pores formed by the plasma spray process are limited in the thickness of the pore layer and result in random pore formation. Vapor deposition techniques for making porous tantalum structures results in articles having a relatively poor bending strength and not suited in many applications where the article has bending force exerted thereon.

Moreover, techniques depositing a powder onto a foam substrate via slurry are limited by the slurry's ability to penetrate and evenly coat the substrate. Other methods such the construction of shapes by the laser sintering of powders are limited to small section by the inherent expense and time-intensive nature of the process.

Thus, there remains a need to provide a porous metal with a controllable pore structure which possesses strength and structural integrity and is free of contamination.

BRIEF SUMMARY OF THE INVENTION

This invention provides methods of manufacturing a porous metal article comprising the steps of combining a metal powder and extractable particles to form a homogenous mixture, forming a composite, extracting the particles to form a metal matrix green article, and sintering the green article. Preferably, the step of extracting the particles comprises exposing the green shape to a water bath.

In one aspect, this invention provides a method of forming granules of metal powder to enhance the homogeneity of the mixture.

In still a further aspect, this invention provides for the forming of metal articles with layers of differing porosity by forming layers containing extractable particulate of varying characteristics. These layers may also be completely free of the extractable particulate to provide a dense layer.

In still a further aspect, this invention allows for the forming of porous metal articles where the matrix green article retains its shape prior to sintering as a result of a binder.

In still a further aspect, this invention allows for the forming of porous metal articles where the matrix green article retains its shape prior to sintering as a result of a deformation of the metal powder particles.

This invention further provides methods of manufacturing a metal article comprising the steps of combining a metal powder with a homogenizing aid to form metal granules, blending the metal granules and an extractable particulate to form a composite, forming the composite into a green article, and sintering the article.

BRIEF DESCRIPTION OF THE SEVERAL VIEWS OF DRAWINGS

For a fuller understanding of the invention, reference is made to the following descriptions taken in conjunction with the accompanying drawings in which.

DETAILED DESCRIPTION OF THE INVENTION

The present invention relates to porous metal articles having porosity characteristics that are determined by an extractable material which is removed prior to sintering and methods to manufacture such porous metal articles.

Powder metallurgy processes are used to form metal articles wherein a portion of the powder being processed is replaced with a pore forming material which is removed prior to sintering to form the desired porosity. The metal articles include articles that are elemental metal, metal alloys, and metal composites. The pore forming material is referred to as an extractable particulate or pore-former.

The metal powder and pore-former are mixed, the article is formed, and the pore-former is extracted. The powder remains to form the metal matrix of material around the pores formed by the extractable particulate. The matrix can then be further shaped and sintered to give the article greater strength.

The use of an extractable particulate to form porosity in an article formed from powder allows control over the pore properties, including pore density, size, distribution, and shape. The pore properties in the final article are determined primarily by the properties of the extractable particulate and, thereby, are tailored by the selection of the extractable particulate. By specifying one or more properties and processing the extractable particulate to reflect the desired pore properties, the present invention allows for the tailoring of the pore character.

The concentration or loading of the extractable particulate in the metal powder determines the porosity and density in the final article. The extent of interconnectivity between the pores is varied by the concentration of the extractable particulate as well as the size of the pore forming material and the matrix forming powder. For example, a compact made using a titanium powder of a −325 mesh as the matrix material and 70 percent or more by volume potassium chloride granules having a mesh size of −20 to +60 will exhibit continuous interconnectivity in the final article. If the potassium chloride granules are reduced in size, interconnectivity will occur at a lesser volume fraction of porosity.

The required interconnectivity and concentration of extractable material used is dictated by the application. Some applications, such as osteointegration and filtration require pore interconnectivity throughout the article. Other applications such as those targeting a reduced weight or density may require a closed pore cell structure. Applications desiring a more porous structure use a larger fraction of extractable material and applications desiring a less porous structure use a lesser fraction of extractable material.

The difference in volume percent porosity of the initial compacted article compared with the sintered article depends on the materials and processing, but is generally less than five percent. Changes in the percent porosity of a compact during processing are due to several factors. The primary factor is that the initial mixing of powders assumes a final density of 100% for the sintered matrix material. However, depending on the subsequent processing and desired final density, sintered densities may vary from 85% to 100% dense. Once the change in volume percent porosity for a particular metal powder and extractable material process has been determined, it remains constant and thus permits the precise tailoring of porosity volume in the final article.

If the percent content of extractable material is too high, it may render the compacted article too fragile to handle between extraction and sintering, or may inhibit compaction of the matrix material. Preferably, the pore-former content will be between 50 and 95 percent. If lower porosity content is desired, it may be advantageous to compact the material to relatively low density in order to allow the easy extraction of the pore-former.

The pore structure and dimensional properties of the final article are tailored by the size and morphology of the extractable particulate. The size and shape properties of the extractable particulate depend on the material used as the extractable particulate. The shape of a pore (for example, spherical, angular or irregular) will correspond to the shape of the extractable particulate used to form it. The size of a specific pore in the final article is proportional to the size of the extractable particulate that is used to form the pore. The proportionality is determined by any shrinkage that may result in the sintering of the metal powder material. The shrinkage encountered during sintering is dictated by the degree to which the matrix is densified. The shrinkage of an article during sintering can be approximated by the following formula:

$$\Delta L/L_i = 1 - (\rho_i/\rho_f)^{1/3}$$

Where:
$\Delta L$=Change in length.
$L_i$=Initial length.
$\rho_i$=Initial density of matrix.
$\rho_f$=Final density of matrix.

This formula does not address changes in shrinkage due to changes in the chemistry of the matrix material such as carbon loss or oxygen pick-up. These are typically slight discrepancies and the actual results are generally within a few percent of the calculated results. Moreover, once the actual shrinkage has been determined for a specific matrix material and manufacturing process, the invention provides for a very consistent and repeatable process with essentially no variability in shrinkage. This allows for the precise control over and ability to tailor the final pore size and shape.

The desired pore size distribution for the final article is determined by the particle size distribution of the extractable particulate. Although some shrinkage may be encountered during processing, the final pore size distribution is directly proportional to the particle size distribution of the extractable particulate. This proportionality is determined by the shrink percentage as discussed above. This relationship allows for the tailoring of articles with very specific pore size distribution by engineering the particle size distribution of the extractable particulate. Methods of tailoring particle size distributions are well known and include milling, grinding, sieving, and air classification. Pore size distributions can be manipulated to produce wide or narrow pore size distributions, as well a bi-modal or multi-modal distributions.

The pore-former characteristics can be varied and combined to achieve the desired pore character. This may include combining several different pore-formers to achieve certain unique properties such as a combination of angular and spherical pores, or a combination of non-continuous pore size distributions.

In addition to considerations related to the predetermination of the desired porosity, there are several process related considerations to be made when selecting an extractable particulate. In a preferred embodiment, the extractable particulate should be compatible with any additional processing steps, it should not leave undesired residue in the final part, it should not react with the matrix material, and it should have adequate strength so as not to be deformed during processing, such as compaction. If the forming route includes elevated temperatures prior to particle extraction (for example, if forming is done via Metal Injection Molding (MIM)), the extractable particulate should exhibit thermal and mechanical stability at those temperatures.

The extractable particulate material should be removable by extraction via a fluid prior to sintering. In a preferred embodiment, the removal is done by dissolving and extracting the pore-former in a water-based system. In this system, ionic bonded materials such as metal salts are desirable as extractable particulates because of ease of removal. Any salt ions should be completely removed from the metal matrix prior to sintering.

Mechanical stability of the extractable article is important. In a preferred embodiment, the extractable particulate material should be selected so it will not deform and store energy during any processing steps (for example, compaction) of the metal powder and extractable particulate mixture. If a material is compressed during the compaction process, then upon removal of the compaction force, any energy stored in the compacted particulate acts upon the compact. This may result in the compact cracking upon removal from the compaction tool or disintegrating during the water extraction step.

According to the present invention, the extractable particulates are preferably water soluble solids, and most preferably potassium chloride, potassium sorbate, sodium chloride, or a mixture thereof.

Some polymeric materials are also suitable for use as extractable particulates depending on melting behavior and solubility. For example, hydroxypropylmethyl cellulose powder may be used for materials that are processed by metal injection molding.

The metal powder used should be chosen based on the desired properties of the final product. The specification of the metal powder should be selected to ensure the article performs predictably during processing. Particles having an irregular, angular, or ligamental nature will deform around or into one another during processing, resulting in better green strength, i.e., the strength of the article after forming the metal powder and extractable material into a shape. For example, when using a compaction technique to form the shape, selecting metal powders with angular characteristics will give the compact adequate green strength. Hydride/dehydride processes for making metal powder result in a desirable angular structure suitable for formation by compaction.

The metal powder is preferably titanium, tantalum, cobalt chrome, niobium, stainless steel, nickel, copper, aluminum, or any alloys thereof. However, it will be apparent that this invention may readily be adapted to other metals by appropriate selection of the extractable material and processing conditions.

In one example for medical implant devices, angular titanium powder of a mesh size between −100 to +635 is be used as the matrix material with potassium chloride particles between 100 and 2000 micron as the extractable particulate. This system may then be formed by compaction.

In another example, potassium sorbate is used as the extractable particulate. Granules of potassium sorbate that are between 600 and 1000 micron in diameter with 17-4 stainless steel metal powder (−22 mesh) are well suited for use with a water-soluble stainless steel feedstock system for use in metal injection molding.

Once the extractable material and metal powder have been selected, the materials are then blended. Blending techniques such as V-blending, mixing on a jar mill, hand blending or use of other known powder mixing techniques can be used.

When the metal powder and the pore-forming material are blended together care must be taken to ensure that the materials form a homogenous mixture irrespective of any variation in particle size and density. In one embodiment, a small amount of a homogenizing aid can be added to help the different materials adhere to each other and create a homogenous mixture. In a preferred embodiment, the homogenization aid can easily be removed after the metal powder and pore-former are compacted. In a most preferred embodiment, the homogenizing aid either (a) is removed by the same fluid used to extract the extractable particulate, or (b) is stable at room temperature and pressure, but will evaporate at elevated temperatures or reduced pressure. Examples of such homogenizing aids include polyethylene glycol (PEG), which reduces segregation and is removable in a water bath prior to thermal processing, and higher alcohols or isoparaffinic solvents, as well as organic liquids, such as acetone, which can easily be removed by evaporation prior to or after compaction.

In one example, titanium powder of a mesh size between −170 to +635 is used as the matrix material, with potassium chloride particles between 100 and 2000 micron, and eight percent by weight of acetone is added, resulting in a homogeneous mixture after V-blending.

In a preferred embodiment, the homogenizing aid is selected to bond to the surface of the metal particles to form metal powder granules of approximately the size corresponding to the spaces between the pore-formers. In a more preferred embodiment, a homogenizing aid that is solid at room temperature is selected for the metal particles. This helps provide greater homogeneity during blending with the pore-former and forming of green articles. The aid can be selected to be removed with the pore-former or it can be selected to be removed after the pore-former is removed.

For example, a water soluble polymer such as medium or high molecular weight PEG is used as a homogenizing aid and added to the metal powder to create granules of the metal powder. These granules can then be mixed with a pore-former to create a feedstock for making porous material. The pore-former may also be treated with a homogenizing aid, typically by coating the pore-former with a second homogenizing aid different from the aid used to coat the metal powder.

In a further preferred embodiment, the homogenizing aid is applied to the metal powder by using a fluid bed, a pan granulator, or a spray drier, and subsequently the material is sieved to select a particular size range of granulates. The specific size range depends on the material and process being used to fabricate the parts. As an example, metal granules below 70 mesh (200 microns) can be used in a system using spherical pore formers between 20 and 60 mesh (850 and 250 microns) to create a homogenous product. The same metal granules also work well with angular pore formers in the between 60 and 100 mesh (150 and 250 microns). The exact size of the metal granule relative to the pore former is not critical as long as the granules are small enough to provide for homogenous blending with the metal granules. The bottom cut of the granulated material is important from the perspective that it is an indicator of the degree of granulation. Substantial amounts of material in the metal granules that are similar in size to the ungranulated material indicates that the granulation process did not affect all of the particles. The detriment of substantial fine material in the granules is that the advantages of granulation are diminished because less of the metal powder is actually granulated. This will result in a less homogenous product. In practice, it is desirable to see less than 20% of granulated product below the average particle size of the metal powder distribution.

Metal granules can be formed from metal powder of a broad size range including at least from 400 microns to below 1 micron. In a preferred embodiment the range of the metal powder is between 150 microns and 5 microns. Metal granules are sized depending on the pore-former used. The size of the granules can range from approximately the size of the metal powder to 2 millimeters. In a preferred embodiment the metal granules are the roughly same size or smaller than the pore former. In a more preferred embodiment the granules are smaller than the pore former.

In a most preferred embodiment, a −200 mesh (−75 micron) angular titanium metal powder made via the hydride-dehydride process is treated with a 20,000 molecular weight polyethylene glycol as the homogenizing aid by dissolving the polymer in water and spraying the solution onto a fluidized bed of titanium powder. In this manner the homogenizing aid is applied to the individual titanium particles which then cling to one another, creating granules. Two weight percent of the polyethylene glycol is applied to the metal particles in the fluid bed and the mixture is dried at 50 degrees Celsius. This material is then sieved to −70 mesh (below 200 microns) to remove any large granules. Spherical potassium chloride having an average diameter of 450 microns is used as the pore-former. The potassium chloride is coated with 0.8 percent by weight PEG 200 as a second homogenizing aid. In this example the PEG 20,000 acts as a homogenizing aid with the metal powder and the PEG 200 act as a homogenizing aid with the pore-former. The resulting feedstock is compacted using an isostatic press at a pressure of 25,000 psi. The resulting compact is machined to the desired shape. After machining, the pore-former and the homogenizing aids are extracted by placing the parts in a water bath and dissolving the potassium chloride and polyethylene glycols.

The selection of the type of homogenizing aid depends in part on the subsequent processing using to form the article. The forming can include compaction and binder assisted forming methods utilizing compression molding, injection molding, compression molding, die compaction and extrusion operations.

For example, if the metal powder and extractable particulate are to be formed via compaction by particle deformation, water soluble waxes such as polyethylene glycols can be used as a homogenizing aid. The PEG can be removed with the pore-former via water extraction since the wax is not needed as a binder to hold the article together after the pore-former is removed.

On the other hand, a wax that is not water-soluble such as paraffin wax, carnauba wax, microcrystalline wax, polypropylene and polyethylene wax may be used as a homogenizing aid if they are intended to also serve as a binder to retain the shape of a formed (green) article. In one embodiment of a process using wax that is not water-soluble, the wax is emulsified. Emulsification combines the wax with water and a surfactant under shear and temperature to create tiny micelles of wax in the water, which are stabilized and kept in suspension by the surfactant. The emulsion surfactants are separate molecules having a polar and non-polar end to each molecule. The non-polar end is attracted to the wax micelle and the polar end is attracted to the water, stabilizing the emulsion. A typical emulsion uses a polyethylene glycol ester or other detergent-like molecule as the surfactant. An advantage of wax emulsions is that wax can be sprayed on the powder much like it could be if the wax were dissolved in a solvent, but without the health and safety concerns of solvents.

In an example of a binder assisted forming method, a −325 mesh spherical titanium powder made via a gas atomization process is treated with a homogenizing aid of a polyethylene wax having a melting point of 90 degrees Celsius. The wax is emulsified in water and sprayed onto the surfaces of the metal particle while the metal particles are suspended in a fluidized bed. In this manner the homogenizing aid is applied to the individual particles which then cling to one another, creating granules. Three weight percent of the wax is applied to the metal particles in the fluid bed and mixture is dried at 50 degrees Celsius. This material is then sieved to −70 mesh to remove any large granulates. Spherical potassium chloride having an average diameter of 450 microns is used as the pore-former. The potassium chloride is coated with 0.8 percent by weight polyethylene glycol 200. In this embodiment the wax acts as a homogenizing aid with the metal powder and the PEG 200 act as a homogenizing aid with the pore-former. The resulting feedstock is compressed using an isostatic press at a pressure of 4500 psi. The resulting article is machined to the desired shape. After machining, the pore-former and the PEG 200 are extracted by dissolution in a water bath. The wax coating the metal particles, which is not soluble in water, remains in the article, binding the metal particles together. This binder is removed by thermally decomposing it prior to sintering.

In this example, the wax performs a dual function of both a homogenizing aid and binder. Spherical powders are difficult to deform and need extremely high pressure to form strong compacts. Because this mixture also uses the wax as a binder and does not rely on particle deformation to create the green strength of the formed articles, the article can be formed at lower pressures. Wax used as a binder takes less pressure to flow and create strength than is needed to deform metal particles. This approach of binder assisted forming of spherical powder may be used with powder injection molding processes, or forming by extrusion, compression molding or die compaction and other processes that use the binder to form the green strength of the article. It is important to note that the binder does not have to melt to create this strength; the relatively low pressure provided is adequate to impart plastic flow to the granules of metal powder. The selection of the specific binder is not limited paraffin waxes, many polymers can also be used, but must be selected with downstream processing in mind.

In another example, mixture of metal granules and pore-former are injection molded into a green article. Here the homogenizing aid used for the granulation should not be soluble in the injection molding binder. It would also be preferred that the granulation binder have a higher melting point than the injection molding binder in order to ensure that the granules to stay intact during compounding and forming steps. For instance, methylcellulose can be used with most known injection molding binders. Methylcellulose is not soluble in many polymer systems and additionally would not be considered melt processable, so the granules have less opportunity to soften or break up as the binder melts or becomes soft.

In systems where the granules are subjected to heat and shear the use of homogenizing aids that are not melt processable, such as many of the modified cellulose materials or polysaccharides may be advantageous because they can be applied in solution to create the granules, and do not melt or have such a high viscosity when they melt, that the granules remain intact throughout processing. Examples of such homogenizing aids for granulation are methylcellulose, agar, polyvinylpyrrolidone, polyvinyl alcohol, and hydroxypropylmethylcellulose. It is not critical that the material be water soluble, but from a safety standpoint, water soluble materials lend themselves more easily to the process, since they preclude the use of organic solvents to disperse the homogenizing aid. In addition to these types of material it is also possible to use a material that is cross-linked after granulation to provide resistance to heat and shear. There are many chemistries that can be used as this type of binder. Conventional cross-linking mechanisms such as thermal or chemical route are useful. Cross-linkable materials such as polyvinyl butyrals, epoxies or modified cellulostics can be used.

In order to ensure good blending and prevent agglomeration, the mixture may be sieved between blending steps or after blending. As another example, in a system using potassium chloride granules having a size range between 250 and 850 micron and a −325 mesh titanium powder and eight weight percent acetone, the mixture can be sieved through a 1000 micron screen to ensure that there are no significant agglomerates.

The homogenizing aid added to the blend to increase homogeneity can be selected to be easily removed before or after the compaction step. There are advantages to either approach. The inclusion of a third material to wet the pore-former and the matrix material can vastly improve homogeneity. If this homogenizing aid is left in the blended materials during the compaction, it can limit the degree to which the materials are compacted because it creates a hydrostatic lock at the limit of the mixture's compatibility. This results in the compacted matrix being slightly less dense than it would have been if the material was not present. In many cases this difference in density is not critical. If however, the highest possible compacted density is required then the homogenizing aid should be removed prior to compaction.

If the homogenization aid remains in the blend during the compacting step, the amount of material used as an aid should be optimized to minimize its effect on compaction while still providing adequate homogenization. In a preferred embodiment, polyethylene glycol (PEG) having a molecular weight of 200 is used to increase homogeneity and is removed after compaction during the water immersion step used to remove the extractable particulate. The amount of PEG 200 used is based on the theoretical density of the mixture of extractable and matrix material if there were no voids present. As an example, a porous titanium implantable device can be formed using potassium chloride granules having a size range between 250 and 850 micron with a −325 mesh titanium powder and 0.05 grams PEG 200 per cubic centimeter of the mixture at theoretical density.

After blending, the metal powder, extractable material, and any homogenizing aid is processed to achieve a desired green shape. This processing can be by known powder consolidation techniques such as die compaction, isostatic pressing, or metal injection molding.

Figure 1:
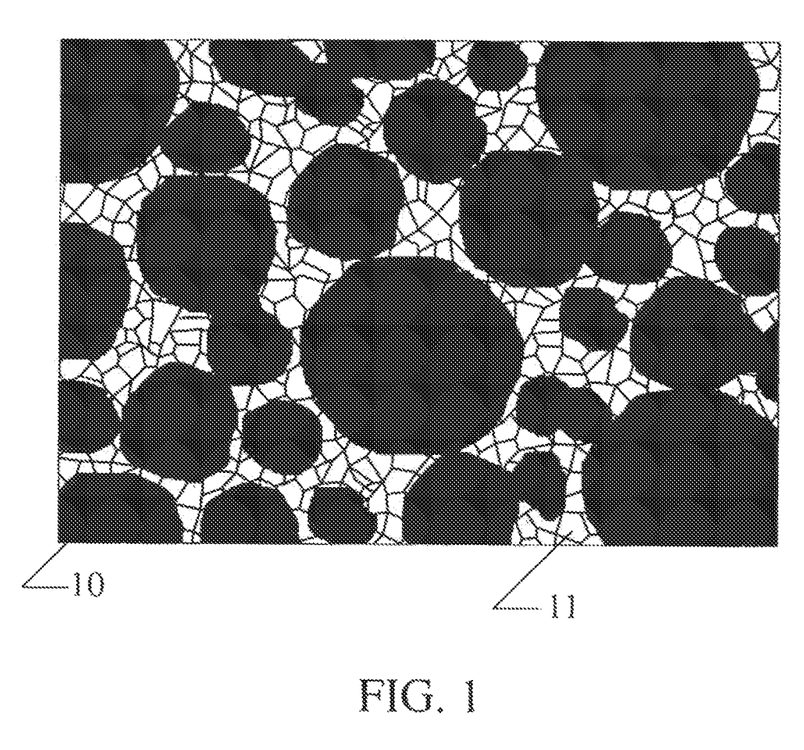
FIG. 1 is a schematic illustration of a compacted mixture illustrating the compacted matrix material and the extractable particles.

FIG. 1 shows an extractable particulate and a matrix powder that have been blended and then consolidated by compacting the mixture into a cylinder. The extractable phase (10) has retained its initial shape after die compaction and is surrounded by the angular matrix powder (11).

After the green article is formed, according to the present invention, the extractable particulate is dissolved out of the article by subjecting the article to an extraction process using a fluid. Dissolving the pore-former in a fluid in which the pore-former is soluble will remove the pore-former from the green article. In a preferred embodiment, a compacted article using a salt as a pore-former is immersed in water, thereby dissolving and removing the extractable particles. Other fluids, including gasses and liquids may be used depending on the dissolution properties of the extractable pore-former. What remains after extraction is an unsintered metal matrix structure surrounding the pores formed by the extractable material.

When using water to dissolve the extractable particulate, the water bath should be deoxygenated to reduce or eliminate the potential for oxidation of the metal powder in the water. This can be done by, for example, bubbling nitrogen through the water, or other known deoxygenating means.

Figure 2:
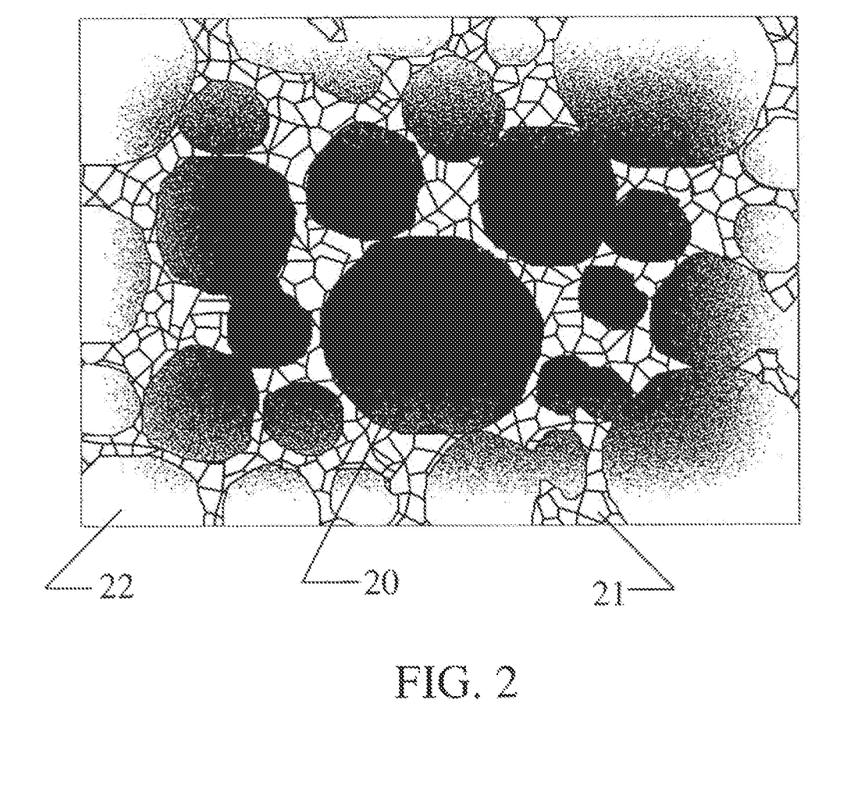
FIG. 2 is a schematic illustration of a compacted mixture with the extractable particles partially extracted.

FIG. 2 shows a schematic of a compacted mixture in accordance with the present invention with the pore-former partially extracted. The compacted matrix powder (21) surrounds the remaining extractable phase (20) and the pores (22) formed during the extraction process. The pores (22) retain the dimensional properties of the extractable particulate used to form them.

By further using a rinsing step after immersion, any amount of pore-former remaining after exposure to the dissolution fluid, can be eliminated or reduced to negligible trace amounts. While certain metal systems may be less sensitive to contamination than others, it is generally desirable to reduce any extractable material remaining in the compacted article to below 2000 parts per million (ppm), and in applications such as medical implants, preferably to below 500 ppm, and most preferably below 200 ppm. As an example, a titanium porous article is made using potassium chloride as the pore-former and has a residual chlorine content in the green article of less than 25 ppm and a potassium content of less than 50 ppm. Such articles will have no significant contamination as a result of the pore-former and are suitable for orthopedic implant applications.

The amount of pore-former extracted can be monitored by known means for analyzing the fluid. As an example, if water is used as the extraction fluid, the amount of extractable material in the water can be measured in ppm by a conductivity meter. Reduction of weight of the green article can also be used to monitor removal of the extractable material.

Figure 3:
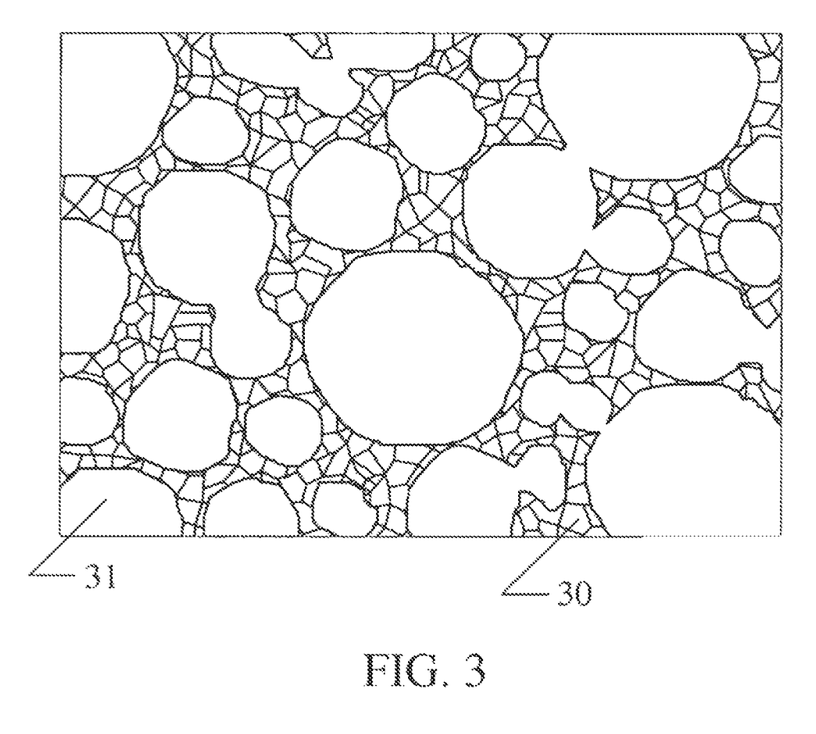
FIG. 3 is a schematic illustration of a metal matrix structure after the extractable particles have been removed.

FIG. 3 represents a schematic of an unsintered metal matrix structure after the pore-former has been removed. The compacted metal matrix (30) defines the porous region (31) formed by the removal of the extractable particulate. The article has adequate green strength to allow handling.

The present invention further provides an economic processing system with no or low environmental impact. When a water extraction approach is used, the water baths are inexpensive to purchase and operate. After processing, the water can be separated from the solute by evaporation or precipitation, allowing for recycling or recovery of the pore-former. Materials preferably used as water soluble pore-formers such as potassium chloride or potassium sorbate do not pose and special handling or safety concerns.

The extraction of the pore-forming material prior to the article being exposed to higher temperatures eliminates the contamination of the matrix material by the pore-former. The mechanical properties and applications of the porous metal dictate the level of contamination permissible in the material. The mechanical properties of titanium and its alloys are greatly reduced by the presence of oxygen, carbon, nitrogen or hydrogen, and titanium becomes increasingly reactive as temperature increases. In an embodiment where a reactive metal is used as the matrix material, it is desirable to remove more than 99.9 percent of the pore-former at low temperatures, typically below 100° C., through fluid extraction.

After extraction of the pore-former, the metal powder matrix structure can be sintered by known means to densify the matrix material. Sintering conditions are determined by the properties of the powder being sintered. The times, temperatures, pressures and atmospheres used in a sintering cycle are selected based on the nature of the material being sintered. Sintering of metal powders is a well understood field and the selection of a sintering cycle can be made by those skilled in the art. Depending on desired properties of the final porous article, the material may be subjected to post sintering processes such as hot isostatic pressing (HIP) to further densify the article.

The present invention includes articles having multiple pore characters such as layers of differing porosity or porous layers on dense substrates. The forming of articles with nonhomogeneous porosity can be accomplished simultaneously or sequentially. An example of a simultaneous route is the die compaction or cold isostatic pressing of multiple layers of material at the same time, where each layer has a pore-former with differing granule properties. This example may also include a layer of metal powder without any extractable material, resulting in a layer of high density. An example of a sequential route is the compaction of a metal powder and extractable particulate mixture onto a solid metal part or substrate. Another example of a sequential route is to take a previously compacted article and compacting a layer onto it. As used herein, the term layer includes any section of material having properties that differ from those surrounding it.

A layer structure according to the present invention has advantages in many applications. A non-porous layer may allow easy fixation of the porous material to a substrate. The non-porous layer may also serve as barrier to isolate the porous material. The non-porous layer can also serve as a mating surface in a thermal management device, and the porous material as a high surface area heat dissipating device. The porous material may serve as kinetic energy dissipating element and the non-porous layer serve to distribute the force of an impact across the porous section.

An article may be formed having layers of differing porosity, providing a part that has a porosity gradient or differing pore character in an article. By co-forming materials with layers containing varying amounts of extractable particulate, an article having areas of differing porosity can be formed. Included in this approach is the forming of a layer that is essentially free of pores. In this manner an article with porous areas on the outside and dense areas on the inside could be formed. Alternatively, an article that is porous on the inside and dense on the outside may also be formed.

Figure 4:
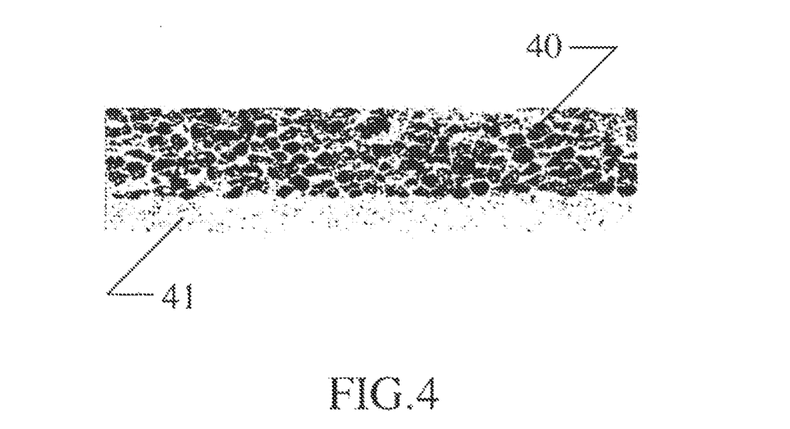
FIG. 4 represents a micrograph at six times magnification showing a cross-section of a layered titanium material made in accordance with the present invention.

FIG. 4 shows an example of an article with layers of varying porosity manufactured according to the present invention. FIG. 4 is a cross-section of an article having a layered nature with alternating section of differing predetermined porosity. A first region (40) has a 85 volume percent porosity and pore sizes in the range of 200-850 microns, a second region (41) is a dense layer which has been sintered to a closed porosity of approximately 95 percent dense.

The article in FIG. 4 is formed by first adding titanium powder of a −325 mesh to a conventional die compaction tool and compacting the material gently so as to distribute it evenly around the tool without significant densification. Then a mixture of 15 volume percent −325 mesh commercially pure titanium metal powder and 85 volume percent −20 mesh potassium chloride with 0.05 g per cc of mixture PEG 200 as a homogenizing aid is added to the tool and compacted at 38,000 psi. The resulting compact has a defined layer of porous material and non-porous material and is processed by removing the extractable phase by immersing the part in water at 60° C., drying the article and sintering in a partial pressure of argon by heating at a rate of 10° C./min to 1255° C. and soaking for two hours. The highly porous region (40) is formed by the mixture of titanium powder and extractable particulate. The second region (41) is of higher density titanium formed by the layer of titanium powder without any extractable particulate.

It is also desirable to form a porous surface onto a preexisting structure or substrate. An example of this is an orthopedic implant. The bulk of the implant is a solid piece that provides the strength of the implant. Porous areas are desired on this piece at areas where bone ingrowth is desired. In one example, a mixture of metal powder and extractable particulate is cold isostatically pressed onto an implant body in the areas where ingrowth is desired.

Figure 5A:
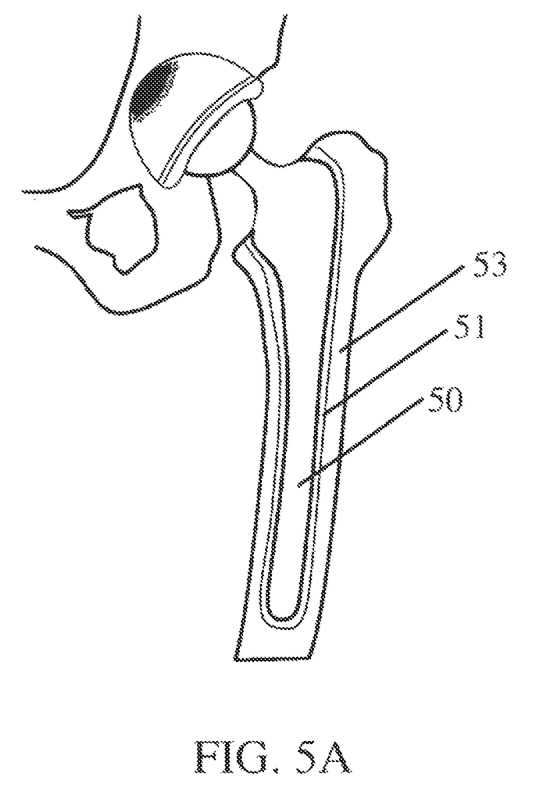
FIG. 5A is a side view of a typical implant in the upper femur in the human body.

An example of an orthopedic implant is shown in FIG. 5A. The implant includes the solid base (50) with a porous outer surface (51). The implant is inserted in the femur bone (53).

Figure 5B:
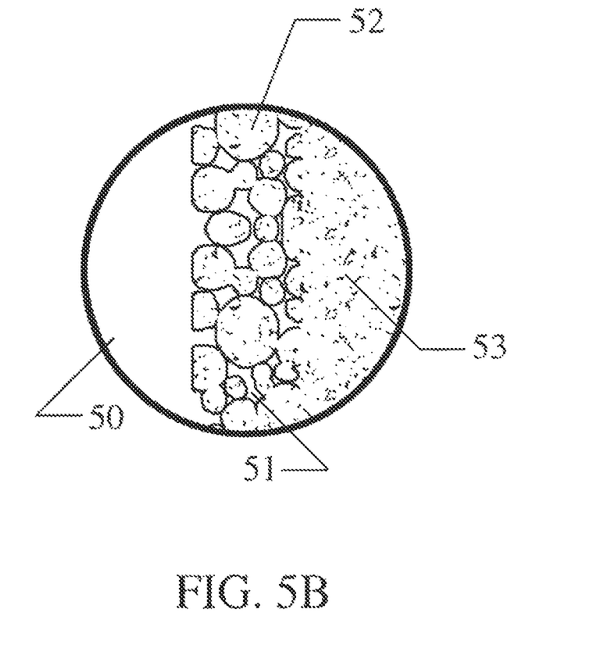
FIG. 5B is a magnified view of the femur in FIG. 5A and shows in detail the interface between the implant and the bone.
Figure 6:
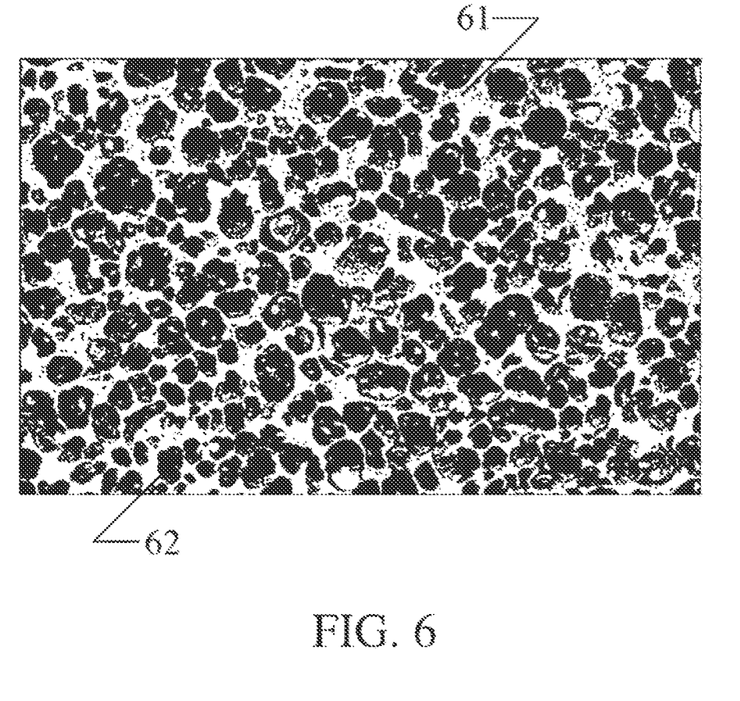
FIG. 6 represents a micrograph at six times magnification showing the surface of porous titanium material made in accordance with the present invention.
Figure 7:
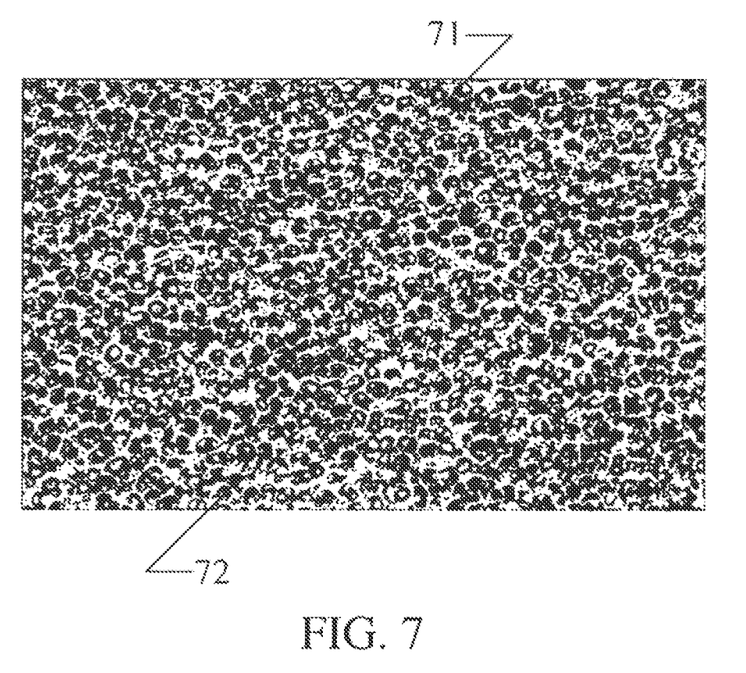
FIG. 7 represents a micrograph at six times magnification showing the surface of porous titanium material made in accordance with the present invention.

FIG. 5B shows is a detailed view of the interface between the implant and the bone. The bone has grown into the open pores (52) of the porous outer surface (51) of the implant. The bone (53) is thereby structurally affixed to the implant (50). This compact having layers of porous material and non-porous material is formed by placing the solid stem of the implant into a rubber tool designed to hold it and also allow the mixture of metal powder and extractable particulate to be poured into a gap around the areas on the stem where a porous area is desired. Then a mixture of 20 volume percent −325 mesh commercially pure titanium metal powder and 80 volume percent −20 mesh potassium chloride with 0.05 g per cc of mixture PEG 200 as a homogenizing aid is poured into the tool and tapped to assure proper filling. The tool is then sealed and cold isostatically pressed at 40,000 psi. The resulting article has a defined layer of porous material and non-porous material. The compacted article is removed from the tool and placed in a water bath at 40° C. to remove the extractable phase. After the removal is complete the part is dried and sintered in a partial pressure of argon at a heating rate of 10° C./min to 1290° C. and held for 1 hour.

When a layer is compacted onto a substrate the close mechanical interface created allows the matrix material to diffusion bond with the substrate material at elevated temperatures. This can typically be done in the same temperature regime used to sinter the matrix material.

When compacting a layer onto a substrate, the layer does not have to be the same material as the substrate. However the materials should be selected to be compatible with the subsequent processes of sintering the matrix and diffusion bonding the layer to substrate the substrate.

In another example, a 3" diameter hemisphere composed of Ti-6Al-4V and having a thickness of 0.25 inches serves as the substrate and is placed in a rubber CIP tool that allows for a 0.25 gap between the hemisphere surface and the tool. The surface of hemisphere that will contact the porous layer has been previously roughened to create a interlock between the substrate and the layer. A mixture of 20 volume percent −325 mesh commercially pure titanium metal powder and 80 volume percent −20 mesh potassium chloride is poured into the tool filling the gap between the substrate surface and the tool, covering the substrate to a thickness of 0.25 inch. The tool is sealed and cold isostatically pressed. The compacted article is then immersed in water between 50 and 60° C. to remove the extractable particulates, and, thereafter, dried. The article is placed in a vacuum furnace at a partial pressure of argon and heated at 10° C./min to 1255° C. and held for two hours. The resulting article has a hemispherical surface that is covered with a layer of titanium having porosity of 80 volume percent and a thickness of 0.2 inches.

The present invention also includes large porous shapes from which a desired shape can be formed using conventional metal forming methods. This technique of forming a desired porosity can also be applied to many binder assisted forming routes such as powder injection molding, extrusion or casting. The specific nature of the binder and forming route must be considered in the selection of an extractable particulate.

For example, in the field of powder injection molding, the binder used to form the powder article is typically removed in two stages. The first stage is typically an extraction stage where a binder phase is removed by solvent extraction, catalytic decomposition, or evaporation. The extractable particulate may be selected to be compatible with the first stage extraction process, eliminating the need for an additional step. For example, if the first stage debinding is done by using water as a solvent, than the extractable particulate can be selected to be water-soluble.

Powder injection molding compounds typically have two components, the powder system and the binder system. The powder system contains the powders that are to be formed and sintered. The binder system is usually composed of various polymers and waxes to allow the forming of the desired shape. The extractable particulate is added to the powder system to create the desired porosity.

The extractable particulate can be combined with commercially available binders. For example, a 17-4 stainless steel article having porosity of 70 percent by volume can be formed by using powder system of the composition:

| | |
|---|---|
| 70% | Potassium chloride |
| 20% | 17-4 master alloy powder, with a particle size less than 20 micron |
| 10% | Carbonyl iron powder |

This powder system can be combined with a commercially available water soluble binder system such as F566 Binder System manufactured by Praxis Technology, Glens Falls, N.Y. The mixing of the materials may be done sequentially to allow proper mixing of the metal powders and the binder prior to adding the extractable particulate. For example, in the above powder system, the 17-4 master alloy powder and the carbonyl iron powder are combined with binder system and mixed until the binder system has melted and a homogeneous mixture is achieved, known as feedstock. The extractable particulate can be added to the feedstock and mixed until homogeneous. The feedstock would have a composition of 92 percent by weight powder (extractable and matrix forming) and eight percent binder.

The necessity for sequential mixing is dictated by the specific binder system used. For instance, the binder system may incorporate emulsified surfactants which contain water that is evaporated during mixing. If the extractable particulate is water soluble, it should be added after the water has been removed from the mixture.

In the preceding example, after the feedstock is mixed, it is injection molded to form the article. The injection molding conditions are based upon the specific binder system used. Using a 17-4 master alloy powder, the melt temperature would be 180-190° C. and the molding pressure about 800 psi. After the article is formed, it is immersed in water at 65-75° C. The use of a water soluble binder system and a water soluble extractable particulate allow the removal of the extractable particulate and the water soluble phase of the binder in the same step. The length of immersion is based upon the size of the molded part. It is helpful to add clean water and removed used water from the bath to maintain an advantageous concentration gradient between the internal section of the part and the water bath. After removal of the bulk of the extractable material, the parts can be rinsed to remove any residual traces of the extractable material.

Following the removal of the extractable particulate the article is processed in a manner consistent with the known art of powder injection molding. In formulations containing a high porosity it may be helpful to presinter the parts in air to allow for strengthening of the interparticle bonds. Oxidation of the carbonyl iron will help to retain the pore structure after the remainder of the binder melts or is thermally decomposed. In the case where air presintering is not feasible, the selection of a powder system using non-spherical powders is helpful in retaining the pore character.

The nature of this invention can be applied to other binder systems used in the binder assisted forming of sinterable powders. The field of binder assisted forming encompasses many different forming techniques such as the injection molding, compression molding, compaction, extrusion, or green machining of articles comprised of a powder and binder mixture.

Although the present invention has been described in terms of examples and presently preferred embodiments, it is to be understood that such disclosure is not to be interpreted as limiting. Various alterations and modifications will no doubt become apparent to those skilled in the art after having read the above disclosure. Accordingly, it is intended that the claims be interpreted as covering all alterations and modifications as fall within the true spirit and scope of the invention.

What is claimed is:

1. A method of making a porous biocompatible metal article, the method comprising:
    a. combining a metal powder with a first homogenizing aid to form metal granules;
    b. blending the metal granules and a water soluble extractable particulate to form a composite;
    c. forming the composite into a green article;
    d. removing the extractable particulate from the green article to form a metal matrix and pore structure; and
    e. sintering the metal matrix and pore structure.

2. The method of claim 1, further comprising combining the extractable particulate with a second homogenizing aid.

3. The method of claim 2, wherein the second homogenizing aid is selected from the group consisting of mineral oil or polyethylene glycol.

4. The method of claim 3, wherein the second homogenizing aid is polyethylene glycol having a molecular weight in the range of 150 to 800.

5. The method of claim 1, wherein the first homogenizing aid is selected from the group consisting of polyethylene glycol, polyethylene wax, polypropylene wax, poly(2-ethyl-2-oxazoline), methylcellulose, agar, polyvinylpyrrolidone, polyvinyl alcohol, hydroxypropylmethylcellulose, and gelatin based materials.

6. The method of claim 5, wherein the first homogenizing aid is polyethylene glycol having a molecular weight of approximately 2000 to 35000.

7. The method of claim 5, wherein the first homogenizing aid IS solid at room temperature.

8. The method of claim 1, wherein the metal powder is selected from the group consisting of: titanium, tantalum, cobalt chrome, niobium, stainless steel, nickel, copper, aluminum, and alloys thereof.

9. The method of claim 1, further comprising the step of sieving the metal granules to a size below 48 mesh.

10. The method of claim 9, wherein the sieving is to below 70 mesh.

11. The method of claim 1, wherein the extractable particulate is selected from the group consisting of: salts, carbonates and sorbates.

12. The method of claim 11, wherein the extractable particulate has a diameter between about 50 and 1000 microns.

13. The method of claim 1, wherein the green article is formed by one of slip casting, compaction, compression, extrusion, or injection molding.

14. The method of claim 13, wherein the compaction deforms the metal powder and provides a shape to the metal matrix and pore structure.

15. The method of claim 1, wherein the extractable particulate is removed by dissolving the extractable particulates in a fluid.

16. The method of claim 15, wherein the fluid is one of water or gas.

17. The method of claim 1, wherein the first homogenizing aid provides a shape to the metal matrix and pore structure by binding the metal powder.

18. The method of claim 1, wherein the porous metal article is an orthopedic implant.

19. A method of making a porous metal article, the method comprising:
   a. combining a metal powder with a first homogenizing aid to form metal granules;
   b. blending the metal granules and a water soluble extractable particulate to form a composite;
   c. forming the composite into a green article;
   d. sintering the green article.

20. The method of claim 19 further comprising removing the first homogenizing aid and the extractable particulate to form a metal matrix and pore structure.

21. The method of claim 19 further comprising combining the green article with a substrate.

22. The method of claim 19, wherein the metal powder is selected from the group consisting of commercially pure titanium and titanium alloys.

23. The method of claim 22, wherein the metal powder is between approximately 1 micron and 150 microns.

24. The method of claim 23 wherein the first homogenizing aid is selected from the group consisting of polyethylene glycol, polyethylene wax, polypropylene wax, poly(2-ethyl-2-oxazoline), methylcellulose, agar, polyvinylpyrrolidone, polyvinyl alcohol, hydroxypropylmethylcellulose, and gelatin based materials.

25. The method of claim 24 wherein combining of the metal powder comprises
   a. dissolving the first homogenizing aid in water to form a solution;
   b. spraying the solution onto a fluidized bed of the metal powder to form the metal granules; and
   c. drying the metal granules at between approximately 30 and 80 degrees Celsius.

26. The method of claim 24 wherein combining of the metal powder comprises
   a. emulsifying the first homogenizing aid in water to form an emulsion;
   b. spraying the emulsion onto a fluidized bed of the metal powder to form the metal granules; and
   c. drying the metal granules at between approximately 30 and 80 degrees Celsius.

27. The method of claim 26 further comprising sieving the granules to −70 mesh.

28. The method of claim 27 wherein the extractable particulate is spherical potassium chloride having an average diameter of 50-600 microns.

29. The method of claim 28 wherein the extractable particulate is coated with a second homogenizing aid.

30. The method of claim 29 wherein the second homogenizing aid is polyethylene glycol having a molecular weight of approximately 200.

31. The method of claim 30 wherein the forming comprising subjecting the composite to a pressure so as to deform the metal particles.

32. The method of claim 31 further comprising removing the first and second homogenizing aids through dissolution in water.

33. The method of claim 30 wherein the forming comprises subjecting the composite to a pressure of less than 20,000 pounds-per-square inch.

34. The method of claim 33 further comprising removing the second homogenizing aid through dissolution in water.

35. A method of making a porous metal article, the method comprising:
   a. emulsifying a first homogenizing aid in water to form an emulsion;
   b. spraying the emulsion onto a fluidized bed of a metal powder to form metal granules, wherein the first homogenizing aid is a water insoluble organic material, and the metal powder is selected from the group consisting of commercially pure titanium powder and titanium ahoy powder between approximately 1 micron and 150 microns;
   c. drying the metal granules at between approximately 30 and 80 degrees Celsius;
   d. sieving the granules to −70 mesh;
   e. combining an extractable particulate with a second homogenizing aid, wherein the extractable particulate is spherical potassium chloride having an average diameter of 50-600 microns, and wherein the second homogenizing aid is polyethylene glycol having a molecular weight of approximately 200;
   f. blending the metal granules and the extractable particulate to form a composite;
   g. shaping the composite to form a green article by applying a pressure of less than 15,000 pounds-per-square inch to the composite;
   h. removing the extractable particulate and the second homogenizing aid through dissolution in water to form a metal matrix and pore structure, wherein the first homogenizing aid provides a shape to the metal matrix and pore structure by binding the metal powder;
   i. removing the first homogenizing aid by heating the metal matrix and pore structure; and
   j. sintering the metal matrix and pore structure.

* * * * *